(12) United States Patent
Brooker et al.

(10) Patent No.: US 9,228,954 B2
(45) Date of Patent: Jan. 5, 2016

(54) METHOD OF DETECTING DEFECTS IN ION EXCHANGE MEMBRANES OF ELECTROCHEMICAL CELLS BY CHEMOCHROMIC SENSORS

(75) Inventors: Robert Paul Brooker, Melbourne, FL (US); Nahid Mohajeri, Rockledge, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 653 days.

(21) Appl. No.: 13/594,163

(22) Filed: Aug. 24, 2012

(65) Prior Publication Data

US 2013/0052745 A1 Feb. 28, 2013

Related U.S. Application Data

(60) Provisional application No. 61/526,873, filed on Aug. 24, 2011.

(51) Int. Cl.
*G01N 21/72* (2006.01)
*G01N 21/78* (2006.01)
*H01M 8/10* (2006.01)

(52) U.S. Cl.
CPC ....... *G01N 21/78* (2013.01); *H01M 2008/1095* (2013.01)

(58) Field of Classification Search
CPC .................. H01M 2008/1095; H01M 4/8657; H01M 4/881; G01N 21/78; G01N 33/0013; Y02E 60/50; Y02E 60/521; C25B 9/04; C25B 9/206

USPC ......................................... 436/164–166, 172
See application file for complete search history.

(56) References Cited

U.S. PATENT DOCUMENTS

| | | | |
|---|---|---|---|
| 6,475,651 B1 * | 11/2002 | Wilkinson et al. | 429/431 |
| 6,895,805 B2 | 5/2005 | Hoagland | |
| 7,560,409 B2 | 7/2009 | Pitts et al. | |
| 8,003,055 B1 | 8/2011 | Muradov | |
| 8,652,993 B2 | 2/2014 | Mohajeri | |
| 2007/0224081 A1 * | 9/2007 | Bokerman et al. | 422/56 |
| 2014/0322631 A1 * | 10/2014 | Klose-Schubert | H01M 4/923 429/528 |

* cited by examiner

*Primary Examiner* — Yelena G Gakh

(74) *Attorney, Agent, or Firm* — Jetter & Associates, P.A.

(57) ABSTRACT

A method of detecting defects in membranes such as ion exchange membranes of electrochemical cells. The electrochemical cell includes an assembly having an anode side and a cathode side with the ion exchange membrane in between. In a configuration step a chemochromic sensor is placed above the cathode and flow isolation hardware lateral to the ion exchange membrane which prevents a flow of hydrogen ($H_2$) between the cathode and anode side. The anode side is exposed to a first reactant fluid including hydrogen. The chemochromic sensor is examined after the exposing for a color change. A color change evidences the ion exchange membrane has at least one defect that permits $H_2$ transmission therethrough.

11 Claims, 3 Drawing Sheets

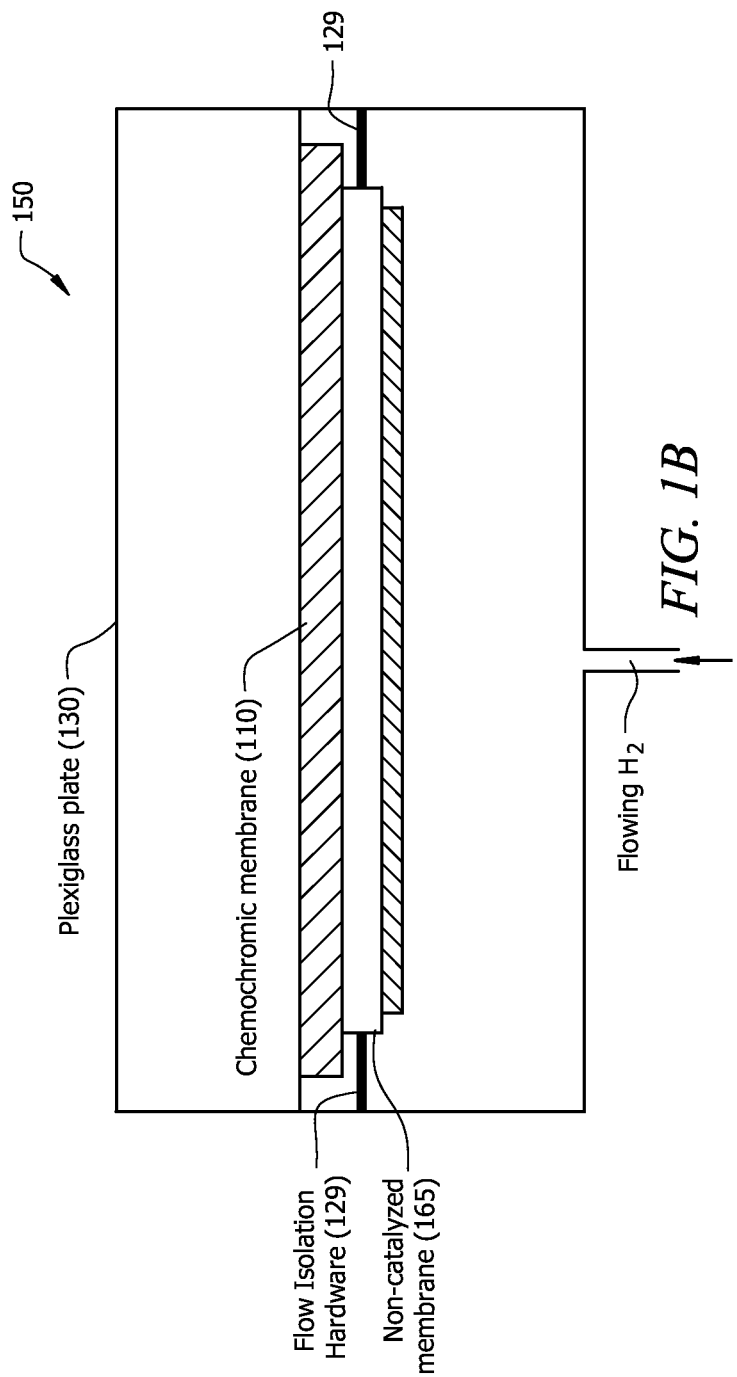

Method (200)

| CONFIGURING A CHEMOCHROMIC SENSOR ABOVE THE CATHODE OF AN ELECTROCHEMICAL CELL THAT INCLUDES AN ASSEMBLY HAVING AN ANODE SIDE AND A CATHODE SIDE WITH AN ION EXCHANGE MEMBRANE IN BETWEEN, AND FLOW ISOLATION HARDWARE LATERAL TO THE ION EXCHANGE MEMBRANE WHICH PREVENTS A FLOW OF HYDROGEN ($H_2$) BETWEEN THE CATHODE AND ANODE SIDE. | — 201 |

| EXPOSING THE ANODE SIDE OF THE ELECTROCHEMICAL CELL TO A FIRST REACTANT FLUID INCLUDING HYDROGEN. | — 202 |

| EXAMINING THE CHEMOCHROMIC SENSOR AFTER THE EXPOSING FOR A COLOR CHANGE. AN IDENTIFIED COLOR CHANGE EVIDENCES THE ION EXCHANGE MEMBRANE HAS AT LEAST ONE DEFECT THAT PERMITS HYDROGEN TRANSMISSION THERETHROUGH. | — 203 |

FIG. 2A

Method (250)

| CONFIGURING A CHEMOCHROMIC SENSOR ABOVE A FIRST SIDE OF A MEMBRANE AND FLOW ISOLATION HARDWARE LATERAL TO THE ION EXCHANGE MEMBRANE WHICH PREVENTS A FLOW OF A REDUCING GAS BETWEEN A SECOND SIDE OF THE MEMBRANE AND THE FIRST SIDE. | — 251 |

| EXPOSING THE SECOND SIDE OF THE MEMBRANE TO THE REDUCING GAS. | — 252 |

| EXAMINING THE CHEMOCHROMIC SENSOR AFTER THE EXPOSING FOR A COLOR CHANGE. AN IDENTIFIED COLOR CHANGE EVIDENCES THE MEMBRANE HAS AT LEAST ONE DEFECT THAT PERMITS REDUCING GAS TRANSMISSION THERETHROUGH. | — 253 |

FIG. 2B

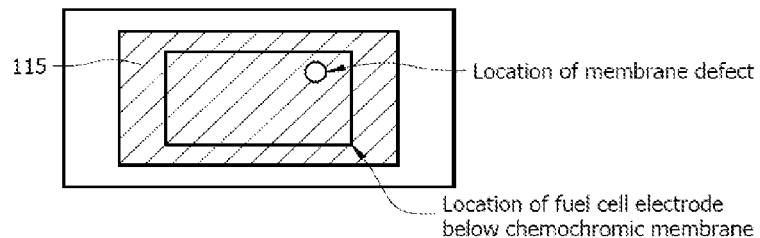

FIG. 3

METHOD OF DETECTING DEFECTS IN ION EXCHANGE MEMBRANES OF ELECTROCHEMICAL CELLS BY CHEMOCHROMIC SENSORS

CROSS-REFERENCE TO RELATED APPLICATIONS

This application claims the benefit of Provisional Application Ser. No. 61/526,873 entitled "CHEMOCHROMIC MEMBRANES FOR MEMBRANE DEFECT DETECTION" filed on Aug. 24, 2011, which is herein incorporated by reference in its entirety.

U.S. GOVERNMENT RIGHTS

This invention was made with U.S. Government support under Florida Hydrogen Initiative contract #DEFC3604GO14225 awarded by the U.S. Department of Energy. The Government has certain rights in the invention.

FIELD

Disclosed embodiments relate to membrane integrity testing, such as for ion exchange membranes used in electrochemical cells.

BACKGROUND

Although fuel cells show promise as future energy delivery devices, they are limited in their ability to be commercialized due to several reasons. Such reasons include the cost of the catalyst, cost of the balance of plant (e.g., saturators, flow controllers, etc.) and the limited durability of the fuel cell ion exchange membrane (hereafter referred to as the "membrane").

Membrane durability is limited by the development of membrane defects during testing and device operation. Examples of membrane defects include, 1) pinholes, where a small hole can develop in the membrane which can allow bulk hydrogen gas ($H_2$) to flow easily from the anode to the cathode, 2) crack formation where a crack develops through the membrane again permitting $H_2$ to flow to the cathode, and 3) membrane thinning, where diffusion of $H_2$ from the anode to the cathode is increased due to a reduction in thickness of the membrane material.

For each case, the unintended presence of $H_2$ at the cathode reduces fuel cell performance significantly, and may even lead to hazardous situations. Increasing the durability of the membrane will make the fuel cells more commercially feasible since they would last longer in the field. However, identifying the factors that affect those failures remains difficult. The ability to locate the specific points of failures in membrane has had limited progress, as typical diagnostic techniques are only able to determine bulk hydrogen crossover. Identifying the location(s) of membrane failures would assist greatly in developing more durable fuel cell membranes.

One known method for identifying the location of membrane failures involves infrared imaging. At membrane defect locations, the respective reactant fluids ($H_2$ and $O_2$) are both present and will exothermically react in the presence of a catalyst generating heat, which is then detected using an infrared thermal detector, thermal imaging device, or a layer of thermally sensitive film positioned in proximity with the membrane.

The infrared method has some significant limitations. These limitations include a requirement that a platinum electrode (or other catalyst) be present over the ion exchange membrane during testing to produce heat. There are also safety concerns because the top of the membrane electrode assembly (MEA) is exposed to the ambient conditions allowing the potential for $H_2$ to enter the ambient environment. Moreover, the localized generation of heat may cause further damage to the membrane.

BRIEF DESCRIPTION OF THE DRAWINGS

FIG. 1B is a schematic of a membrane testing configuration that shows a chemochromic membrane in an arrangement for a non-catalyzed membrane (i.e. for a membrane without a catalyst layer or GDL), according to an example embodiment.

FIG. 2A is a flow chart that shows steps in an example chemochromic method for detecting defects in an ion exchange membrane of an electrochemical cell, according to an example embodiment.

FIG. 2B is a flow chart that shows steps in another example chemochromic method for detecting defects in a membrane, according to an example embodiment.

FIG. 3 is an example depicted scanned image obtained using the membrane testing configuration shown in FIG. 1A.

DETAILED DESCRIPTION

Figure 1A:
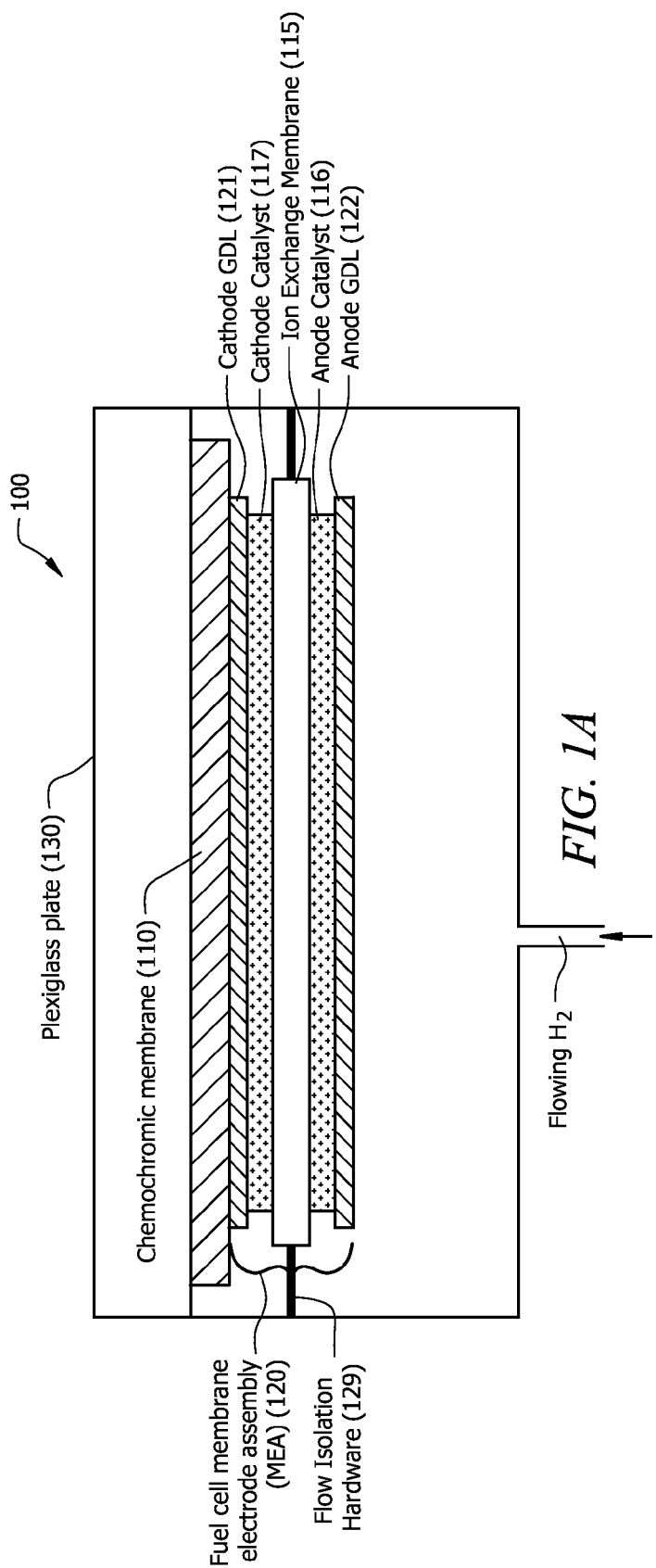
FIG. 1A is a schematic of a membrane testing configuration that shows a chemochromic membrane in an arrangement for sensing defects in an ion exchange membrane situated above a cathode gas diffusion layer (GDL) of a fuel cell membrane electrode assembly (MEA), according to an example embodiment.

Disclosed embodiments in this Disclosure are described with reference to the attached figures, wherein like reference numerals are used throughout the figures to designate similar or equivalent elements. The FIGs are not drawn to scale, and they are provided merely for illustration. Several aspects are described below with reference to example applications for illustration.

It should be understood that numerous specific details, relationships, and methods are set forth to provide a full understanding of the disclosed embodiments. One having ordinary skill in the relevant art, however, will readily recognizes that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Disclosed embodiments include location-specific identification of ion exchange membrane defects through the use of chemochromic membranes as chemochromic sensors which are sensitive to $H_2$ and other reducing gases (e.g., carbon monoxide, and hydrocarbons). The functional reaction of a typical chemochromic sensor is an oxidation catalyst such as palladium oxide (PdO) being reduced to the elemental metal (e.g., metallic palladium), with a concomitant color change from brown to black in the case of PdO. This reduction can be achieved through exposure to $H_2$ or other reducing gas, with a resultant generation of water. As used herein membrane defects can include pinholes, ruptures, tears, or localized regions of reduced thickness and/or higher permeability relative to the bulk ion exchange membrane, and other defects in the membrane which can cause fluids, such as $H_2$, to leak through the thickness of the ion exchange membrane.

To increase the dispersion of the oxidation catalyst (e.g., a PdO catalyst) to reduce the amount of catalyst needed for a detectable color change, titania or other materials can be used as a catalyst support, where the catalyst is deposited on the support. In an embodiment the chemochromic sensor comprises a metal oxide or metal salt support, and metal comprising particles on the support including at least first particles comprising a palladium compound. The palladium compound can comprise PdO or palladium hydroxide. The metal comprising particles can further comprise second particles comprising a precious metal group (PMG) metal or a PMG metal compound, where in one embodiment the PMG metal is not palladium. The PMG metal compound can comprise ruthenium oxide ($RuO_2$) or platinum oxide (PtO) in particular non-limiting embodiments. For example, in one particular support arrangement, PdO is deposited onto the surface of titania support particles, forming a "chemochromic pigment".

This pigment can be suspended (e.g., encapsulated) in a polymeric matrix that is permeable to $H_2$ or other reducing gas, such as silicone rubber or silicon resin, which can then be cast into thin films. In this embodiment the gas permeable polymer provides a continuous phase that completely encapsulates the metal comprising particles and optional support.

The response of the pigment-doped chemochromic membrane is dependent on several factors, namely the permeability of $H_2$ (or other reducing gas) within the polymer matrix, and the reaction rate of the pigment (e.g., rate of PdO reduction to Pd metal). The permeability of $H_2$ (or other reducing gas) within the polymer matrix is a function of the polymer's native properties, as well as cast chemochromic membrane thickness. The reaction rate for the pigment (e.g., PdO) reduction is dependent on $H_2$ (or other reducing gas) concentration, as well as on the pigment coverage of the support. For example, due to the high degree of oxidation on titania, the reduction of PdO generally exhibits an induction period prior to proceeding with complete reduction. This induction period results in longer wait times between exposure to $H_2$ (or other reducing gas) and color change of the pigment from light brown to black.

It has been found that palladium compound oxidation catalysts such as PdO when doped with a PMG metal or PMG metal compound on a support provides supported oxidation catalysts which oxidize a reducing gas (e.g., $H_2$ carbon monoxide, and hydrocarbons) with significantly increased sensitivity (i.e. rate of color change) as compared to the same palladium compound catalyst without a dopant. The PMG metal or PMG metal compound may also improve the selectivity to $H_2$ (e.g., become more selective to $H_2$ than to CO). Disclosed PMG metals can comprise gold, silver, or platinum group metals, such as ruthenium, rhodium, osmium, iridium, and platinum. For example, depositing both platinum and PdO onto a support such as titania has been found to dramatically reduce the induction period, resulting in considerably quicker responses when the final chemochromic membrane is exposed to $H_2$. It is postulated that the platinum assists in $H_2$ oxidation, which in turn will increase the rate of PdO reduction.

As described herein, chemochromic membranes were used as provided, i.e. they were prepared and cast. Since the chemochromic membranes are sensitive to reducing gases such as $H_2$, they can be used in one embodiment for fuel cells to locate areas of $H_2$ crossover to the cathode. In particular, the chemochromic membranes may be used to detect defects in membranes before or after operation in a fuel cell. Identification of the defect's location may permit mitigation strategies, such as positioning the defect in a location outside the active area of the fuel cell where it would not impact durability.

FIG. 1A is a schematic of a membrane testing configuration 100 that shows a chemochromic membrane 110 in an arrangement for sensing defects in an ion exchange membrane situated above a cathode gas diffusion layer (GDL) 121 of a fuel cell membrane electrode assembly (MEA) 120. As known in the art, all chemical and electrochemical reactions happen in MEA 120. A polymeric ion exchange membrane 115 with layers of catalyst (usually Pt) on both sides provides an anode catalyst 116 and a cathode catalyst 117 that is sandwiched by anode side GDL 122 and the cathode side GDL 121. A GDL is generally a porous carbon paper and its function is to feed the active gases to the catalyst layer and transport the byproduct (mainly water) to the outside of the fuel cell. It is noted that the anode catalyst 116 and cathode catalyst 117 shown are optional for disclosed membrane testing, unlike the known infrared method.

Membrane testing configuration 100 includes flow isolation hardware lateral to the membrane for directing flowing gas (isolating hardware) 129 which prevents a flow of $H_2$ between the cathode side and anode side. The isolation hardware 129 used for disclosed membrane defect testing is non-specific, so long as it permits flowing $H_2$ (e.g., 4% $H_2$ and 96% argon) along the anode side of the fuel cell MEA 120, while preventing $H_2$ to flow to the cathode side. Thus, the presence of $H_2$ on the cathode side should only result from defects within the ion exchange membrane 115. In one example embodiment, the isolation hardware 129 used was the anode hardware from conventional fuel cell testing, with a PLEXIGLASS plate 130 that can be placed over the cathode GDL 121, allowing uniform compression on the chemochromic membrane 110 and the MEA 120.

In operation, once the hardware is assembled, the anode side can be purged with a suitable gas such $N_2$ for several minutes, $H_2$ is then applied to the anode side for a period of time, such as 15 seconds. In this time, $H_2$ flows through any defects in the ion exchange membrane 115 and begins reducing the Pd ions (or other pigment) in the chemochromic membrane 110. After at least about 10 to 20 seconds, the $H_2$ can be removed and the hardware again purged with $N_2$. Once purged, the chemochromic membrane 110 can be removed and examined for the presence of any dark spots, indicative of the presence of metallic palladium, which in turn indicates the location of membrane defects.

Testing may be performed at an elevated pressure across the polymeric ion exchange membrane 115. For example, the polymeric ion exchange membrane 115 may be tested for leaks at a pressure differential which is greater than that which is likely to be experienced in normal operation. Applying a higher pressure differential across the polymeric ion exchange membrane 115 will tend to force more $H_2$ through any defects present, and will thus increase the sensitivity of the method to allow detection of smaller defects.

FIG. 1B is a schematic of a membrane testing configuration 150 that shows a chemochromic membrane 110 in an arrangement for a non-catalyzed membrane 165 (i.e. for a membrane without a catalyst layer and GDL), according to an example embodiment. The operation and testing procedure described above relative to membrane testing configuration 100 for polymeric ion exchange membrane 115 is also generally applicable to non-catalyzed membrane 165. Although a GDL is not shown on the side of the non-catalyzed membrane 165 opposite to the chemochromic membrane 110 (the supply side), a GDL can be added to membrane testing configuration 150 to improve distribution of $H_2$ on the supply side of the non-catalyzed membrane 165.

FIG. 2A is a flow chart that shows steps in an example chemochromic method 200 for detecting defects in an ion exchange membrane of an electrochemical cell, according to an example embodiment. The electrochemical cell includes an assembly having an anode side and a cathode side with the ion exchange membrane in between. In configuration step 201 a chemochromic sensor is placed above the cathode and flow isolation hardware lateral to the membrane which prevents a flow of $H_2$ between the cathode and anode side. Step 202 comprises exposing the anode side of the electrochemical cell to a first reactant fluid including $H_2$. In step 203 the chemochromic sensor is examined after the exposing step for a color change. An identified color change evidences the ion exchange membrane has at least one defect that permitted $H_2$ transmission therethrough.

FIG. 2B is a flow chart that shows steps in an example chemochromic method 250 for detecting defects in a membrane. In configuration step 251 a chemochromic sensor is placed above a first side of the membrane and flow isolation hardware lateral to the membrane which prevents a flow of a reducing gas between a second side of the membrane and the first side. Step 252 comprises exposing the second side of the membrane to the reducing gas. In step 253, following the exposing step the chemochromic sensor is examined for a color change. An identified color change evidences the ion exchange membrane has at least one defect that permitted reducing gas transmission therethrough.

An example of the chemochromic effect is shown in depicted scanned image of FIG. 3, which was obtained using the arrangement shown in the membrane testing configuration 100 shown in FIG. 1A. The depicted scanned image of FIG. 3 was compared with a known infrared method for determining pinholes and other defects in ion exchange membranes. In this example, $H_2$ was left flowing for 20 seconds.

As can be seen in FIG. 3, a region of darkening is evident along the left-hand edge (note that the visible side of the chemochromic membrane is that side which was in contact with the MEA, i.e. it's been flipped over). Although the region of darkening was identified by eye, identifying the location(s) of membrane defects may be performed using an automatic means, such as a camera with a computing device (e.g. processor) that evaluates the degree of darkness in the image obtained.

Results from a disclosed method were then compared with results from the known infrared method which relies on the combustion of $H_2$ with air ($O_2$) to generate heat, which can then be imaged using an infrared camera. The infrared approach was used for the same MEA as was tested by the disclosed chemochromic membrane method. It was seen that the chemochromic membrane provided comparable results as the infrared image, with the MEA defects appearing to be essentially the same sizes in the same locations.

Disclosed methods using chemochromic membranes for MEA defect location have several significant advantages over the known infrared method. Firstly, the infrared imaging method requires that a platinum electrode (or other catalyst) be present over the ion exchange membrane. Without the platinum electrode, no heat will be generated, as the $H_2$ without a catalyst will not combust with $O_2$. Subsequently, the infrared technique cannot identify MEA defects that occur outside the active area of the electrode. The disclosed chemochromic membrane method is not limited in this regard, and does not need a catalyst layer attached to the ion exchange membrane.

Secondly, the disclosed chemochromic membrane method is inherently safer as compared to the infrared method, as the entire assembly is sealed for the disclosed chemochromic method. When using the infrared method, the top of the MEA is exposed to the ambient conditions, allowing the potential for $H_2$ to enter the ambient environment. Thirdly, the chemochromic membrane method is inherently passive, with no risk damaging the MEA further. The infrared method exposes the MEA to conditions no worse that when the MEA is employed within a fuel cell, which implies no further damage occurs to the MEA. However, the local generation of heat using the infrared method may further damage, and exacerbate the defect.

Although the primary anticipated use for disclosed embodiments is to determine ion exchange membrane defects for fuel cells, disclosed embodiments can be used more generally for the detection and location of defects in ion-exchange membranes and separators used in other types of electrochemical cells, such as electrolytic cells, and chloro-alkali cells, batteries, in electrowinning, and also for membranes employed in plate-and-frame humidification portions of solid polymer electrochemical fuel cell stacks. Moreover, disclosed embodiments can broadly include any application that requires membranes be impermeable to gases for proper function, from dialysis membranes to ZIPLOC bags, which could all benefit from chemochromic membrane defect detection provided by disclosed embodiments.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

We claim:

1. A method of detecting defects in an ion exchange membrane of an electrochemical cell including an assembly comprising an anode side and a cathode side with said ion exchange membrane in between, comprising:
configuring a chemochromic sensor layer above said cathode in an enclosure with flow isolation hardware between said ion exchange membrane and walls of said enclosure which prevents a flow of hydrogen ($H_2$) between said cathode side and said anode side, wherein the flow of $H_2$ is received from an inlet of said enclosure on said anode side,
exposing said anode side to a first reactant fluid including said $H_2$, and
examining said chemochromic sensor layer after said exposing for a color change, wherein said color change evidences said ion exchange membrane has at least one defect that permits hydrogen transmission therethrough during said exposing.

2. The method of claim 1, wherein said method further comprises identifying a position of said defect on said ion exchange membrane.

3. The method of claim 1, wherein said electrochemical cell comprises a fuel cell and said assembly comprises a membrane electrode assembly (MEA).

4. The method of claim 1, wherein said chemochromic sensor layer comprises:
a support comprising a metal oxide or a metal salt, and
metal or metal compound particles on said support including at least first particles comprising PdO or palladium hydroxide.

5. The method of claim 4, wherein said metal comprising particles further comprise second particles comprising a precious metal group (PMG) metal or PMG metal compound.

6. The method of claim 5, wherein said PMG metal is not palladium.

7. The method of claim 5, wherein said PMG metal comprises at least one of gold, silver, and a platinum group metal other than palladium.

8. The method of claim 4, wherein said palladium compound comprises palladium oxide or palladium hydroxide.

9. The method of claim 4, wherein said chemochromic sensor layer further comprises a gas permeable polymer that provides a continuous phase that completely encapsulates said metal comprising particles and said support.

10. The method of claim 9, wherein said gas permeable polymer comprises silicone rubber.

11. The method of claim 1, wherein said examining is performed automatically.

* * * * *